United States Patent
Haley

(10) Patent No.: US 12,233,158 B2
(45) Date of Patent: Feb. 25, 2025

(54) ORALLY ADHERING LOZENGES CONTAINING SOLUBLE DIETARY FIBER

(71) Applicant: Quest Products, LLC, Pleasant Prairie, WI (US)

(72) Inventor: Jeffrey T. Haley, Mercer Island, WA (US)

(73) Assignee: Quest Products, LLC, Pleasant Prairie, WI (US)

( * ) Notice: Subject to any disclaimer, the term of this patent is extended or adjusted under 35 U.S.C. 154(b) by 0 days.

(21) Appl. No.: 17/831,150

(22) Filed: Jun. 2, 2022

(65) Prior Publication Data

US 2022/0387309 A1    Dec. 8, 2022

Related U.S. Application Data

(60) Provisional application No. 63/196,930, filed on Jun. 4, 2021.

(51) Int. Cl.

| | |
|---|---|
| *A61K 9/00* | (2006.01) |
| *A23L 33/21* | (2016.01) |
| *A23P 10/28* | (2016.01) |
| *A23P 20/20* | (2016.01) |
| *A23P 30/10* | (2016.01) |
| *A61K 31/05* | (2006.01) |
| *A61K 31/465* | (2006.01) |
| *A61K 31/522* | (2006.01) |
| *A61K 31/728* | (2006.01) |
| *A61K 36/28* | (2006.01) |

(52) U.S. Cl.
CPC ............ *A61K 9/0056* (2013.01); *A23L 33/21* (2016.08); *A23P 10/28* (2016.08); *A23P 20/20* (2016.08); *A23P 30/10* (2016.08); *A61K 31/05* (2013.01); *A61K 31/465* (2013.01); *A61K 31/522* (2013.01); *A61K 31/728* (2013.01); *A61K 36/28* (2013.01); *A23V 2002/00* (2013.01)

(58) Field of Classification Search
None
See application file for complete search history.

(56) References Cited

U.S. PATENT DOCUMENTS

| 8,865,133 | B2 | 10/2014 | Haley | |
|---|---|---|---|---|
| 8,945,606 | B2 | 2/2015 | Haley | |
| 9,688,779 | B2 | 6/2017 | Haley | |
| 9,789,061 | B2 | 10/2017 | Haley | |
| 2004/0156930 | A1* | 8/2004 | Haley | .................. A61K 31/43 514/192 |
| 2009/0169489 | A1 | 7/2009 | Haley | |

(Continued)

OTHER PUBLICATIONS

Images of Orajel® Benzocaine 15 mg Protective Mouth Sore Discs believed to be publicly available at least as of 2007 (2 pages).

*Primary Examiner* — Walter E Webb

(74) *Attorney, Agent, or Firm* — Fitch, Even, Tabin & Flannery LLP

(57) ABSTRACT

Orally adhering lozenges comprising soluble dietary fiber are provided herein. The orally adhering lozenges provided herein may be in the form of tablet-type lozenges comprising compressed powders and/or granules in at least two layers. The orally adhering lozenges include at least 30% soluble dietary fiber. The orally adhering lozenges also include an adhesive component to adhere the lozenge inside the mouth. The orally adhering lozenges are also low in cariogenic sugar, non-resistant starch, and polyols.

20 Claims, 1 Drawing Sheet

(56) References Cited

U.S. PATENT DOCUMENTS

| | | |
|---|---|---|
| 2010/0285098 A1 | 11/2010 | Haley |
| 2012/0251622 A1 | 10/2012 | Haley |
| 2015/0024092 A1* | 1/2015 | Strehlow ................ A23P 20/10 426/103 |
| 2015/0110851 A1 | 4/2015 | Haley |
| 2015/0147555 A1 | 5/2015 | Haley |
| 2015/0320787 A1 | 11/2015 | Haley |
| 2016/0184236 A1 | 6/2016 | Haley |
| 2017/0296487 A1 | 10/2017 | Haley |
| 2018/0296466 A1 | 10/2018 | Haley |
| 2021/0022998 A1 | 1/2021 | Haley |

\* cited by examiner

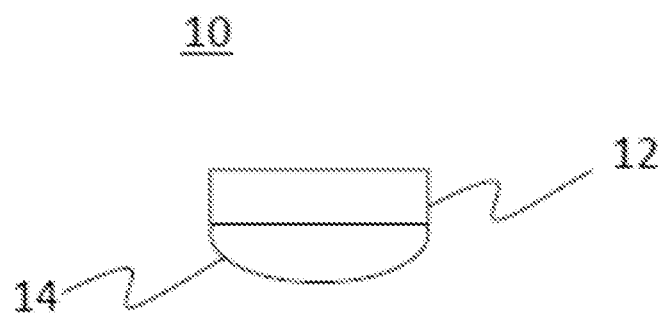

ORALLY ADHERING LOZENGES CONTAINING SOLUBLE DIETARY FIBER

CROSS-REFERENCE TO RELATED APPLICATIONS

This application claims the benefit of U.S. Provisional Application No. 63/196,930, filed Jun. 4, 2021, which is incorporated herein by reference in its entirety.

FIELD

This application relates generally to orally adhering lozenges, particularly, to orally adhering bi-layer tablet type lozenges.

BACKGROUND

Lozenges, also called troches, have been known for centuries. In recent decades, improved lozenges have been prepared with an orally adhesive layer on one side of the lozenge so that it will adhere to a surface in the mouth. Such orally adhering lozenges are discreet for the user. Because the adhered lozenge is exposed to saliva on only one side of the lozenge, the lozenges may dissolve more slowly than non-adhering lozenges.

Lozenges generally require at least one water soluble bulking agent to achieve a slow rate of dissolution. The oldest known bulking agent is sugar in the form of glucose, fructose, sucrose, or other mono or di-saccharides. However, such sugars are cariogenic and promote growth of bacteria that cause tooth decay. Starch has also been used, but enzymes in the mouth convert starch to cariogenic sugar. In recent decades, sugar or starch as a bulking agent has been replaced by polyols, mainly sorbitol, xylitol, erythritol, and maltitol, all of which dissolve slowly like cariogenic sugars but advantageously do not promote tooth decay. However, polyols can cause gut discomfort.

SUMMARY

Provided herein are orally adhering lozenges for release of a target component in the mouth. In one approach, the lozenge comprises at least two layers, including an adherent layer and a non-adherent layer. The adherent layer comprises an adhesive component and the non-adherent layer comprises a mixture of a soluble dietary fiber and a target component. The lozenge comprises at least 30% soluble dietary fiber by weight of the lozenge, as can be measured when analyzed by AOAC method 991.43. In some embodiments, the lozenge comprises at least 40% soluble dietary fiber by weight of the lozenge when analyzed by AOAC method 991.43.

In one aspect, the orally adhering lozenge comprises less than 4% cariogenic sugar by weight of the lozenge when analyzed by AOAC method 982.14. In another aspect, the orally adhering lozenge comprises less than 2% cariogenic sugar by weight of the lozenge when analyzed by AOAC method 982.14. In another aspect, the orally adhering lozenge comprises less than 30% polyol by weight of the lozenge when analyzed by AOAC method 982.14. In another aspect, the orally adhering lozenge comprises less than 20% polyol by weight of the lozenge when analyzed by AOAC method 982.14. In yet another aspect, the orally adhering lozenge comprises less than 4% cariogenic sugar and less than 30% polyol by weight of the lozenge when analyzed by AOAC method 982.14.

The adhesive component may comprise one or more of acacia gum, gelatin, gum Arabic, alginate, starch, pectin, polyvinyl acid, polyvinylpyrrolidone, carboxymethylcellulose (CMC), hydroxymethylcellulose, polyacrylic acid, and carbomer.

The soluble dietary fiber may comprise comprises one or more of dextrin, resistant dextrin, resistant maltodextrin, inulin, enzyme resistant starch, enzyme resistant modified starch, polydextrose, psyllium, non-starch polysaccharide, polycarbophil, chitin, pectin, guar gum, partially hydrolyzed guar gum, locust bean gum, carrageenan, xanthan gum, konjac gum, beta-glucan, oligosaccharide, and fructooligosaccharide.

The target component may comprise one or more of a flavor and an active pharmaceutical ingredient. In one approach, the target component comprises one or more of a flavor, antibiotic, anesthetic, analgesic, antiviral, aspirin, anti-inflammatory, antacid, cannabidiol, antifungal, nicotine, caffeine, chamomile, hyaluronan, vitamin, mineral, plant extract, and herbal supplement.

The orally adhering lozenges may further comprise one or more of a lubricant, pH adjusting agent, and binder.

Provided herein is also a method of preparing a lozenge for the oral release of a target component. In one approach, the method comprises: forming a first powder mixture; placing the first powder mixture in a die; inserting an upper punch into the die and pressing the upper punch to compress the first powder to form a first layer of compressed powder; forming a second powder mixture; placing the second powder mixture into the die on top of the first layer of compressed powder and pressing the upper punch to compress the second powder mixture to form a bilayer lozenge, wherein either the first or second powder mixture comprises a combination of soluble dietary fiber and at least one target component, and the other of the first or second powder mixture comprises an adhesive component, and wherein the bi-layer lozenge includes at least 30% soluble dietary fiber by weight of the lozenge when analyzed by AOAC method 991.43.

In one approach, the bilayer lozenge comprises at least 40% soluble dietary fiber by weight of the lozenge when analyzed by AOAC method 991.43.

In another approach, the bilayer lozenge comprises less than 4% cariogenic sugar by weight of the lozenge when analyzed by AOAC method 982.14. In another aspect, the bilayer lozenge comprises less than 2% cariogenic sugar by weight of the lozenge when analyzed by AOAC method 982.14. In yet another approach, the bi-layer lozenge comprises less than 30% polyol by weight of the lozenge when analyzed by AOAC method 982.14. In another aspect, the bilayer lozenge comprises less than 20% polyol by weight of the lozenge when analyzed by AOAC method 982.14. In yet another aspect, the orally adhering lozenge comprises less than 4% cariogenic sugar and less than 30% polyol by weight of the lozenge when analyzed by AOAC method 982.14.

In one approach, the soluble dietary fiber comprises one or more of dextrin, resistant dextrin, resistant maltodextrin, inulin, enzyme resistant starch, enzyme resistant modified starch, polydextrose, psyllium, non-starch polysaccharide, polycarbophil, chitin, pectin, guar gum, partially hydrolyzed guar gum, locust bean gum, carrageenan (particularly in kappa form), xanthan gum, konjac gum, beta-glucan, oligosaccharide, and fructooligosaccharide.

BRIEF DESCRIPTION OF THE DRAWING

The FIGURE shows a side view or cross section of an exemplary orally adhering lozenge in the form of a bilayer lozenge.

DETAILED DESCRIPTION

Described herein are oral adhering lozenges comprising soluble dietary fiber as a soluble bulking agent. The lozenges may also comprise one or more insoluble bulking agents in the form of particles or powders. However, to achieve a satisfactory dissolution profile, such insoluble component should be mixed with soluble ingredients, such as a soluble dietary fiber or a soluble carbohydrate (e.g., sugars or polyols).

The oral adhering lozenges described herein may be provided in the form of tablet-type lozenges comprising compressed powders and/or granules in at least two layers. The adhering lozenges dissolve in the mouth upon contact with saliva to facilitate the release of one or more ingredients, such as a target component (e.g., a therapeutic agent or flavor). The orally adhering lozenges may be adhered onto any surface in the month, such as the mouth mucosa, braces, teeth, or gums, and the components of the lozenge are released into saliva in the mouth or into the mucosa. Erosive forces at the surface of the lozenge, such as from rubbing against mucosa, teeth, and the tongue, and dissolution of the soluble bulking agent in saliva will progressively expose and release particles forming the lozenge.

The lozenges provided herein are low in cariogenic sugars and polyols. Though polyols are not readily converted to acids by bacteria in the mouth and, thus, do not contribute to tooth decay, it is desirable to limit the polyol content because polyols may cause adverse gastrointestinal effects. It has been advantageously found that soluble dietary fiber can be a complete or partial replacement for other bulking agents, such as sucrose and/or polyols, in lozenges without compromising the dissolution properties of the lozenge, the release of any target components from the lozenge, the sensory qualities of the lozenge, or rendering the lozenge cariogenic.

It is further contemplated that the inclusion of soluble dietary fiber in the lozenge may provide other beneficial results, including promoting desirable physiological effects such as laxation, blood cholesterol attenuation, and/or blood glucose attenuation.

In one approach, the lozenges may be provided in the form of a bilayer lozenge. In one particular approach, the bilayer lozenge is a bilayer orally adhering lozenge comprising at least a first adherent layer and a second non-adherent layer. When the lozenge is provided in the form of an orally adhering bilayer lozenge, the lozenge includes at least 30 wt % soluble dietary fiber (in another aspect, at least 40 wt % soluble dietary fiber, in another aspect at least 50 wt % soluble dietary fiber), less than 4 wt % cariogenic sugar (in another aspect, less than 2 wt % cariogenic sugar, in another aspect less than 1 wt % cariogenic sugar), less than 30 wt % polyol (in another aspect, less than 25 wt % polyol, in another aspect less than 20 wt % polyol, in another aspect less than 15 wt % polyol, in another aspect less than 10 wt % polyol, in another aspect less than 5 wt % polyol), and less than 4 wt % non-resistant starch (in another aspect, less than 2 wt % non-resistant starch, in another aspect less than 1 wt % non-resistant starch), by weight of the lozenge.

In yet another approach, the lozenges may be provided with a plurality of layers, such as at least three layers. When the lozenge is provided with a plurality of layers, the lozenge includes at least 30 wt % soluble dietary fiber (in another aspect, at least 40 wt % soluble dietary fiber, in another aspect at least 50 wt % soluble dietary fiber), less than 4 wt % cariogenic sugar (in another aspect, less than 2 wt % cariogenic sugar, in another aspect less than 1 wt % cariogenic sugar), less than 30 wt % polyol (in another aspect, less than 25 wt % polyol, in another aspect less than 20 wt % polyol, in another aspect less than about 15 wt % polyol, in another aspect less than 10 wt % polyol, in another aspect less than 5 wt % polyol), and less than 4 wt % non-resistant starch (in another aspect, less than 2 wt % non-resistant starch, in another aspect less than 1 wt % non-resistant starch), by weight of the lozenge, with the percentages being by weight of the entire lozenge.

The layers of lozenges having two or more layers may be relatively equal in thickness and/or total weight. In other approaches, the layers of lozenges having two or more layers may have different thicknesses and/or different total weights. At least in some approaches, a non-adherent layer may be thicker and/or have a higher total weight than the adherent layer.

The lozenge will generally release the target component over a long dissolution time, such as 5 minutes to 8 hours. Typically, the lozenge will erode over time and completely dissolve. The ingredients of the lozenge should be selected to have a dissolution time appropriate for the target component being delivered. For example, it may be desired for the lozenge to deliver the target component relative quickly (e.g., in about 10 minutes) or it may be intended for the lozenge to be used in the mouth during sleeping such that a desired dissolution of 6-8 hours is preferred.

Soluble Dietary Fiber

The lozenge includes a soluble dietary fiber. The soluble dietary fiber may function, for example, as a soluble bulking agent in the lozenge. The soluble dietary fiber bulking agent may be provided in a mixture with a water-insoluble component and advantageously provide a suitable dissolution profile despite the presence of the insoluble component. As used herein, the term "soluble dietary fiber" refers to dietary fiber that dissolves in water. As used herein, the term "dietary fiber" refers to fiber that generally passes through the mouth and small intestine without being broken down by human digestive enzymes. The soluble dietary fiber useful herein may include fermentable fiber (i.e., fiber partially or completely fermented by gastrointestinal microbiota in the large intestine to produce physiologically beneficial byproducts, such as short chain fatty acids, and gases) or non-fermentable fiber (e.g., psyllium, inulin, and resistant starch). As used herein, the term soluble dietary fiber does not include cellulose, which in its natural form is insoluble, and does not include human modified cellulose which, while it may dissolve in water, has an undesirable dissolution profile and mouth feel. Soluble dietary fiber can promote beneficial physiological effects including laxation, blood cholesterol attenuation, and blood glucose attenuation.

Soluble dietary fiber may include, for example, certain water-soluble polysaccharides and oligosaccharides. Generally, plant fiber materials useful herein comprise soluble dietary fiber and are substantially non-cellulosic. In some aspects, the soluble dietary fiber useful herein includes non-cellulosic carbohydrates having a degree of polymerization of at least 10 monomeric units.

As used herein, the term "soluble dietary fiber" specifically includes resistant starch, which is a carbohydrate that is not digested in the small intestine but is fermented in the large intestine like other soluble dietary fiber. Resistant starch is starch that has been modified to not be converted to sugars by amylase enzymes. Any suitable soluble dietary fiber may be used in the lozenge. Exemplary soluble dietary fibers include one or more of dextrin, resistant dextrin, resistant maltodextrin, inulin, enzyme resistant starch, enzyme resistant modified starch, polydextrose, psyllium, non-starch polysaccharide, polycarbophil, chitin, pectin, guar gum, partially hydrolyzed guar gum, locust bean gum, carrageenan (particularly in kappa form), xanthan gum, konjac gum, beta-glucan, oligosaccharide, and fructooligosaccharide. Advantageously, dietary fibers are not broken down to glucose in the small intestine and do not significantly raise glucose levels after consumption. Advantageously, many types of soluble dietary fibers may function as binders as well as bulking agents. For example, dextrin, guar gum, partially hydrolyzed guar gum, carrageenan, and xanthan gum may assist in binding the ingredients together in the lozenge. Therefore, further binding agents may not need to be added. Soluble dietary fibers are generally effective to bind to themselves when compressed in a tablet press and can be made into lozenges with a tablet press.

Exemplary commercially available sources of soluble dietary fiber include LOGIFIBER® dextrin (which the manufacturer claims to be about 2% sugar and about 89% soluble fiber), HI-MAIZE® 260 enzyme resistant corn starch from Ingredion (which the manufacturer claims to be less than about 0.1% sugar and about 61% soluble fiber), PROMITOR® Soluble Fibre from Tate & Lyle (which the manufacturer claims to be about 85% soluble dietary fiber and less than about 2% sugar), NUTRIOSE® 06 dextrin of wheat (FB) or maize (FM) origin from Roquette (which the manufacturer claims to be less than about 0.5% mono or di saccharide sugars and at least about 82% soluble fiber), and FIBERSOL®-2 (which the manufacturer claims to be about 2% sugar and about 90% soluble fiber).

In one approach, the non-adherent layer of bilayer or multilayer lozenges may include at least 40 wt % soluble dietary fiber, in another aspect at least 50 wt % soluble dietary fiber, in another aspect at least 60 wt % soluble dietary fiber, in another aspect at least 70 wt % soluble dietary fiber, by weight of the non-adherent layer.

For purposes herein, the amount of soluble dietary fiber in the lozenge can be determined by AOAC Official Method 991.43, which is incorporated herein by reference.

Insoluble Components

In addition to the soluble components, the orally adhering lozenges may also comprise one or more water insoluble components. In some aspects, the water insoluble component may function as a bulking agent. For example, the water insoluble component may include magnesium stearate, calcium carbonate, insoluble fiber (e.g., inulin, cellulose, and lignin), or any safely ingestible insoluble powder. It is generally preferred that any insoluble components have a particle size small enough to not adversely impact the mouthfeel of the orally adhering lozenges.

By mixing the insoluble component with water soluble components (e.g., the soluble dietary fiber and any sugars or polyols), a satisfactory dissolution profile may be achieved. In one approach, the insoluble component and water-soluble components are provided in a homogeneous mixture.

Cariogenic Sugars

The lozenges provided herein contain no or low amounts of cariogenic sugars. In one aspect, the lozenges include less than 4 wt % cariogenic sugar, in another aspect less than 2 wt % cariogenic sugar, in another aspect less than 1 wt % cariogenic sugar. For example, cariogenic sugars include any of monosaccharides, disaccharides, glucose, dextrose, fructose, sucrose, maltose, lactose, xylose, and galactose.

For purposes herein, the amount of cariogenic sugar in the lozenge can be determined by AOAC Official Method 982.14, which is incorporated herein by reference.

Polyols

The lozenges provided herein also contain no or low amounts of polyol. In one aspect, the lozenges include less than 30 wt % polyol, less than 25 wt % polyol, in another aspect less than 20 wt % polyol, in another aspect less than 15 wt % polyol, in another aspect less than 10 wt % polyol, and in another aspect less than 5 wt % polyol by weight of the lozenge. It is generally preferred that the amount of polyol in the lozenges be limited so that there are no adverse effects, such as abdominal discomfort, bloating, or laxative effect.

Polyols (i.e., sugar alcohols) include, for example, xylitol, erythritol, sorbitol, mannitol, polyglycitol, maltitol, isomalt, and lactitol. If included in the lozenges, the polyol may be provided in the form of a solid at room temperature. In another approach, the polyol may be provided in the form of a powder comprising polyol crystals.

For purposes herein, the amount of polyol in the lozenge can be determined by AOAC Official Method 982.14, which is incorporated herein by reference.

Non-Resistant Starch

The lozenges provided herein also contain no or low amounts of non-resistant starches. In one aspect, the lozenges include less than 4 wt % non-resistant starch, and in another aspect less than 2 wt % non-resistant starch. As used herein, the term "non-resistant starch" refers to starch that is broken down into glucose and absorbed in the small intestine when digested.

It is contemplated that soluble plant fiber material may include small amounts of impurities in the form of polyols or sugars, in addition to soluble dietary fiber. However, the amounts of polyol and/or sugars contained within soluble plant fiber materials added to the lozenges should be in keeping with the maximum amounts of polyol and cariogenic sugars by weight of the lozenges as discussed herein.

Target Component

The lozenge provided herein also includes one or more target components released from the lozenge when the lozenge erodes and/or dissolves in the mouth. The target component may be any ingredient or combination of ingredients included in the lozenge for therapeutic effect and/or flavor, such as for treating a disease or condition, ameliorating a symptom of a disease or condition, or delivering a needed vitamin or mineral for oral absorption. For example, the target component may increase salivation for treatment of gastric reflux or dry mouth. In another approach, the target component may treat conditions such as halitosis, mucositis, stomatitis, oral aphthous ulceration, vestibulitis, lichen planus, and Behcet's syndrome, among others. However, the disease or condition being treated need not be limited to oral diseases or conditions.

In one approach, suitable target components include therapeutic agents, active pharmaceutical ingredients ("APIs"), flavors, or any combinations thereof. Suitable APIs include those that can be delivered orally by absorption through mucous membranes of the oral cavity. The target component may be a therapeutic agent, such as in the form of an inorganic compound, organic compound, peptide, protein, carbohydrate, amino acid, fatty acid, mineral, vitamin, and any combination thereof. Exemplary target components include, for example, antibiotic, anesthetic, analgesic, antiviral, aspirin, anti-inflammatory, antacid, cannabidiol (CBD), antifungal (e.g., Nystatin, Clotrimazole), nicotine, caffeine, chamomile, hyaluronan (also known as hyaluronic acid), vitamin, mineral, plant extract, or herbal supplement.

In another approach, the target component may also be a flavor, such as cinnamon (e.g., ground cinnamon bark), mint (e.g., mint oil), almond, lavender, rose, spearmint, peppermint, wintergreen, eucalyptus, ginger, lemongrass, fruit flavor, fruit essence, fruit extract, or any other flavor. The flavor may also include a specific flavor compound, such as α-irisone, allyl caproate, anethole, iso-amyl acetate, iso-amyl butyrate, benzyl alcohol, butyl cinnamate, carvone, cinnamic alcohol, citral, gamma-decalactone, β-damascenone, decanal, decanol, γ-undecalactone, diacetyl, dihydroanethole, ethyl acetate, ethyl butyrate, ethyl cinnamate, ethyl salicylate, eucalyptol, ethyl maltol, eugenol, geranial, geraniol, heliotropine, 4-cis-heptenal, ionone, limonene, linalool, maltol, 1-menthyl acetate, menthone, methyl anthranilate, methyl-p-tert-butyl phenyl acetate, methyl cinnamate, methyl salicylate, neral, nerol, gamma-nonalactone, oxanone, octanol, octanal, phenylethyl alcohol, propenyl guaethol, α-terpineol, thymol, or a combination thereof. The flavor may also include a high intensity sweetener, such as, for example, one or more of aspartame, sucralose, saccharin, acesulfame potassium (Ace-K), neotame, advantame, cyclamate, alitame, neohesperidin dihydrochalcone, N—[N-[3-(3-hydroxy-4-methoxyphenyl)propyl]-L-a-aspartyl]-L-10 phenylalanine 1-methyl ester, N—[N-[3-(3-hydroxy-4-methoxyphenyl)-3-methylbutyl]-L-aaspartyl]-L-phenylalanine 1-methyl ester, N—[N-[3-(3-methoxy-4-hydroxyphenyl)propyl]L-a-aspartyl]-L-phenylalanine 1-methyl ester, and salts thereof, and steviol glycoside sweeteners, such as rebaudioside A, rebaudioside B, rebaudioside C, rebaudioside D, rebaudioside E, rebaudioside F, dulcoside A, dulcoside B, rubusoside, stevioside, and steviolbioside. Some high intensity sweeteners have been found to contribute off-flavor to products, particularly when used in increasing amounts. Therefore, at least in some approaches, the particular high intensity sweetener and the amount of the high intensity sweetener should be selected so as to not provide undesirable bitter flavor to the lozenge. In some approaches, the amount of flavor included in the orally adhering lozenges is effective to trigger salivation.

The flavor may be provided in a variety of forms, such as in a powder (e.g., extruded, spray-dried, agglomerated, freeze-dried, and encapsulated flavorings). If not in powder form, the flavor component may be combined with a carrier (such as acacia gum, dextrin, maltodextrin, or cellulose gum) to form a powder.

The amount of target component included in the lozenges may vary widely depending on the nature of the target component and the dose to be delivered. At least in some approaches, the amount of target component included in the lozenges is an amount effective to have a therapeutic benefit.

Adhesive Component

The bilayer lozenges described herein further comprises an orally adhesive component to adhere the lozenge to a surface in the mouth. The adhesive component need not be adhesive when in dry or granular form, such as when present in a lozenge that is not in use, but the adhesive component should at least have adhesive properties when wetted by saliva in the user's mouth.

Any suitable consumable oral adhesive may be used. For example, acacia gum adheres very well to teeth and gingiva and may act as an adhesive in the adherent layer. Alternatively, the lozenge may comprise one or more other adhesive components, such as gelatin, gum Arabic, alginate, starch, pectin, polyvinyl acid, polyvinylpyrrolidone, polyacrylic acid, and carbomers (e.g., CARBOPOL® polymers from Lubrizol).

The adhesive component should be included in an amount effective to adhere the lozenge to the desired surface in the human user's mouth. In one approach, the adherent layer includes at least 60 percent adhesive component by weight of the adherent layer, in another aspect at least 70 percent adhesive component, in another aspect at least 75 percent adhesive component, and in yet another aspect at least 80 percent adhesive component, in order to provide sufficient adhesiveness to the lozenge for adhering to the inside of a user's mouth. In a preferred aspect, the adhesive component is acacia gum.

Additional Ingredients

The lozenge may further include a variety of other ingredients, such as one or more binders, fillers, salts, buffers, coatings, and combinations thereof. These ingredients can be selected to provide desired appearance, flow, hardness, taste, and/or compression characteristics to the lozenge or one or more layers thereof. For example, the lozenge may include a thin water-soluble coating to maintain an attractive appearance and to minimize the release of dust from the lozenge. For purposes herein, any coatings are not considered a "layer," as the term "layer" is used to refer to compressed powder layers.

The lozenge may also include a lubricant. The lubricant may act to lubricate the process of pushing tablets out of the dies of a tablet press. Any suitable lubricant may be used in the lozenge. In some embodiments, the lubricants may comprise one or more of calcium stearate and magnesium stearate.

The lozenge may also include a pH adjusting agent. Any suitable pH adjusting agent may be used in the lozenge to provide a desired pH upon mixing with saliva in the mouth. In one approach, the pH adjusting agent may comprise an alkalizer (i.e., base) to adjust the pH of the lozenge or layers thereof when mixed with saliva in the mouth. It is well known that acidic pH can be damaging to teeth. Therefore, it may be desired that the lozenge has a neutral or basic pH upon dissolving or otherwise disintegrating in saliva (such as when 1 part lozenge is dissolved in 10 parts water). In one approach, the alkalizer may be calcium carbonate, but any alkalizer that that does not adversely impact the lozenge, such as microbial stability, chemical stability, textural stability, or appearance of the lozenge may be used. Other examples include magnesium carbonate, sodium bicarbonate, potassium bicarbonate, sodium carbonate, magnesium hydroxide, aluminum hydroxide, $C_7H_5HiO_4$, and combinations thereof.

Suitable binder materials to strengthen the non-adherent layer of the lozenge include, for example, acacia gum, polyvinyl pyrrolidone, maltodextrin, sorbitol, lactose, and cellulose gum. To ensure the lozenge erodes at a desired rate in the mouth, the lozenge may include a binder that dissolves slowly in saliva or mucosa. Optionally, the binder may be made with slowly dissolving hydrocolloids so that the lozenge lasts in the mouth for at least about ten minutes and up to about six hours. Suitable binders that dissolve slowly in saliva include collagen, gelatin, agar, starch (such as corn starch or pregelatinized starch), and combinations thereof.

Notwithstanding the above discussion of additional components suitable for the lozenges, when adding any additional components, the amounts of polyol, cariogenic sugar, and non-resistant starch coming in as major or minor ingredients in those components should be controlled in keeping with the maximum amounts of non-resistant starch, polyol, and cariogenic sugar by weight of the lozenges as discussed herein.

Tablet Type Lozenges

The oral adhering lozenges provide herein may be provided in the form of tablet-type lozenges comprising compressed powders and/or granules in at least two layers.

In one approach, the tablet type lozenge is in the form of a bilayer tablet including a non-adherent layer and an adherent layer. At least in some approaches, the non-adherent layer includes some or all of the target component to be released as the lozenge degrades in the mouth and the adherent layer includes the adhesive component for adhering the lozenge to the surface in the mouth. In some approaches, a weight of the non-adherent layer may be the same as a weight of the adherent layer. In another approach, a weight of the non-adherent layer may be greater than a weight of the adherent layer.

Method of Making

The oral adhering lozenges described herein can be made by a method including forming a first powder mixture by mixing soluble dietary fiber and at least one target component, and pressing the first powder mixture to form a non-adherent layer. The method further includes forming a second powder mixture for the adherent layer containing an adhesive component, and pressing the second powder mixture to form an adherent layer. As shown in the FIGURE, lozenge 10 includes layers 12 and 14. In one approach, layer 12 may be the non-adherent layer and layer 14 may be the adherent layer.

It is contemplated that the second powder mixture may comprise additional components or, in some aspects, may only include the adhesive component, such as acacia gum. The adherent layer becomes adhesive when wetted by saliva in a human mouth. In this manner, the oral adhering lozenge is configured to adhere to a surface of the human mouth when wetted by saliva in the mouth.

In one approach, the ingredients for the respective layers of the oral adhering lozenges are supplied in free-flowing powders or granules suitable for flowing from one or more hoppers into a tablet press. Powders and/or granules may be pressed into the respective layers of the lozenge using the tablet press. In some approaches, the lozenge may be manufactured using a bilayer tablet press having lower punches in dies and upper punches aligned above the dies. Powders and/or granules may be fed to the tablet press using a hopper or any other suitable feed system.

In one particular approach, a method of making lozenges for release of a target component in the mouth comprises: providing a tablet press with lower punches in dies and upper punches aligned above the dies; placing a first powder mixture in the dies, where the first powder mixture comprises soluble dietary fiber and at least one target component; inserting the upper punches into the dies; pressing the punches together to compress the powders; adding into the dies a second powder comprising an adhesive component; compressing the second powder with the upper punch; and ejecting the tablets from the dies.

In some approaches, a force within the range of about 20 kilonewtons to about 45 kilonewtons and, in another aspect, within the range of about 25 kilonewtons to about 40 kilonewtons, and in another aspect in the range of about 25 kilonewtons to about 35 kilonewtons is applied, to the two layers of powder mixtures to form the lozenge.

The lozenge may be formed in any suitable shape and size. In one particular approach, the lozenge may have a size of about 8 to 15 mm in diameter, a thickness of about 3 to about 8 mm, and a total weight of about 350 to about 900 mg.

To further illustrate the present disclosure, an example is given herein. It is to be understood that this example is provided for illustrative purposes and is not to be construed as limiting the scope of the present disclosure.

EXAMPLE

An exemplary formulation for a non-adherent layer of a tablet type lozenge for slowly releasing mint flavor and sweetness is provided in Table 1.

TABLE 1

| Ingredient | Amount (wt %) |
|---|---|
| Sucralose | 0.2 |
| Klucel ® Nutra D Cellulose Gum from Ashland Products (Binder Component) | 0.9 |
| Magnesium Stearate (Lubricant) | 0.9 |
| Calcium Carbonate (pH Adjusting Agent) | 1.5 |
| Mint Flavor (mint oil (20%) on powder carrier (80%)) | 18.3 |
| NUTRIOSE ® Dextrin from Roquette (nominally 82% soluble fiber) | 78.2 |
| Total | 100.0 |

A lozenge made with the above formulation may be made as a tablet type bilayer lozenge. A bilayer lozenge can be made by providing a layer of an adhesive component, such as acacia gum powder, on one side to form a bilayer lozenge having an adherent side (layer) and a non-adherent side (layer).

In one approach, the bilayer lozenge may be a round tablet having a diameter of 12 mm and a thickness of about 6 mm. In one approach, the adherent side is nearly flat with a shallow dimple in the center and the non-adherent side is domed (i.e., convex on one side and concave on the other side).

The bilayer lozenge made using the formulation in Table 1 can be formed using a bilayer tablet press having a die with a cupped lower punch and a nearly flat upper punch.

First, a mixture of the ingredients in Table 1 is added to the lower punch of the bilayer tablet press and an upper punch of the bilayer tablet is used to compress the mixture. Next, a powdered adhesive component is added to the lower punch of the bilayer tablet press and the upper punch then presses the adhesive component to form the bilayer tablet. For example, a force of about 35 kilonewtons may be used. The resulting tablet has a thickness that is approximately uniform while the layer with the formulation of Table 1 is thicker in the center and thinner at the edges (i.e., on the domed non-adherent side).

It is to be understood that the ranges provided herein include the stated range and any value or sub-range within the stated range. For example, a range of 5 wt % to 15 wt % should be interpreted to include not only the explicitly recited limits of range of 5 wt % to 15 wt %, but also to include individual values, such as 6.35 wt %, 7.5 wt %, 10 wt %, 12.75 wt %, 14 wt %, etc., and sub-ranges, such as 7 wt % to 10.5 wt %, 8.5 wt % to 12.7 wt %, 9.75 wt % to about 14 wt %, etc. Furthermore, when "about" is utilized to describe a value, this is meant to encompass minor variations (up to +/−10%) from the stated value.

All percentages and ratios are calculated by weight unless otherwise indicated. All percentages and ratios are calculated based on the total weight of the layer or composition unless otherwise indicated.

Reference throughout the specification to "an example," "one example," "another example," "some examples," "other examples," and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:

1. An orally adhering lozenge for release of a target component in the mouth, the lozenge comprising at least two layers formed of compressed powders, the lozenge comprising:
    an adherent layer comprising an adhesive component; and
    a non-adherent layer comprising a mixture of at least 60% soluble dietary fiber by weight of the non-adherent layer and a target component,
    wherein the lozenge comprises at least 30% soluble dietary fiber by weight of the lozenge when analyzed by AOAC method 991.43.

2. The orally adhering lozenge of claim 1, wherein the lozenge comprises at least 40% soluble dietary fiber by weight of the lozenge when analyzed by AOAC method 991.43.

3. The orally adhering lozenge of claim 1, comprising less than 4% cariogenic sugar by weight of the lozenge when analyzed by AOAC method 982.14.

4. The orally adhering lozenge of claim 1, comprising less than 2% cariogenic sugar by weight of the lozenge when analyzed by AOAC method 982.14.

5. The orally adhering lozenge of claim 1, comprising less than 30% polyol by weight of the lozenge when analyzed by AOAC method 982.14.

6. The orally adhering lozenge of claim 1, comprising less than 20% polyol by weight of the lozenge when analyzed by AOAC method 982.14.

7. The orally adhering lozenge of claim 1, comprising less than 4% cariogenic sugar and less than 30% polyol by weight of the lozenge when analyzed by AOAC method 982.14.

8. The orally adhering lozenge of claim 1, wherein the adhesive component comprises one or more of acacia gum, gelatin, gum Arabic, alginate, starch, pectin, polyvinyl acid, polyvinylpyrrolidone, carboxymethylcellulose (CMC), hydroxymethylcellulose, polyacrylic acid, and carbomer.

9. The orally adhering lozenge of claim 1, wherein the soluble dietary fiber comprises one or more of dextrin, resistant dextrin, resistant maltodextrin, inulin, enzyme resistant starch, enzyme resistant modified starch, polydextrose, psyllium, non-starch polysaccharide, polycarbophil, chitin, pectin, guar gum, partially hydrolyzed guar gum, locust bean gum, carrageenan, xanthan gum, konjac gum, beta-glucan, oligosaccharide, and fructooligosaccharide.

10. The orally adhering lozenge of claim 1, wherein the target component comprises one or more of a flavor and an active pharmaceutical ingredient.

11. The orally adhering lozenge of claim 1, wherein the target component comprises one or more of a flavor, antibiotic, anesthetic, analgesic, antiviral, aspirin, anti-inflammatory, antacid, cannabidiol, antifungal, nicotine, caffeine, chamomile, hyaluronan, vitamin, mineral, plant extract, and herbal supplement.

12. The orally adhering lozenge of claim 1, further comprising one or more of a lubricant, pH adjusting agent, and binder.

13. A method of preparing a bilayer lozenge for the oral release of a target component, the method comprising:
    forming a first powder mixture;
    placing the first powder mixture in a die;
    inserting an upper punch into the die and pressing the upper punch to compress the first powder to form a first layer of compressed powder;
    forming a second powder mixture;
    placing the second powder mixture into the die on top of the first layer of compressed powder and pressing the upper punch to compress the second powder mixture to form a bilayer lozenge,
    wherein either the first or second powder mixture comprises a combination of at least 60% soluble dietary fiber by weight of the powder mixture and at least one target component, and the other of the first or second powder mixture comprises an adhesive component,
    wherein the bi-layer lozenge includes at least 30% soluble dietary fiber by weight of the lozenge when analyzed by AOAC method 991.43.

14. The method of claim 13, wherein the bilayer lozenge comprises at least 40% soluble dietary fiber by weight of the lozenge when analyzed by AOAC method 991.43.

15. The method of claim 13, wherein the bilayer lozenge comprises less than 4% cariogenic sugar by weight of the lozenge when analyzed by AOAC method 982.14.

16. The method of claim 13, wherein the bilayer lozenge comprises less than 2% cariogenic sugar by weight of the lozenge when analyzed by AOAC method 982.14.

17. The method of claim 13, wherein the bi-layer lozenge comprises less than 30% polyol by weight of the lozenge when analyzed by AOAC method 982.14.

18. The method of claim 13, wherein the soluble dietary fiber comprises one or more of dextrin, resistant dextrin, resistant maltodextrin, inulin, enzyme resistant starch, enzyme resistant modified starch, polydextrose, psyllium, non-starch polysaccharide, polycarbophil, chitin, pectin, guar gum, partially hydrolyzed guar gum, locust bean gum, carrageenan, xanthan gum, konjac gum, beta-glucan, oligosaccharide, and fructooligosaccharide.

19. An orally adhering lozenge for release of a target component in the mouth, the lozenge comprising at least two layers, the lozenge comprising:
    an adherent layer comprising an adhesive component; and
    a non-adherent layer comprising a mixture of at least 60% soluble dietary fiber by weight of the non-adherent layer and a target component,
    wherein the lozenge comprises at least 30% soluble dietary fiber by weight of the lozenge when analyzed by AOAC method 991.43, and
    wherein the soluble dietary fiber comprises one or more of dextrin, resistant dextrin, resistant maltodextrin, inulin, enzyme resistant starch, enzyme resistant modified starch, polydextrose, psyllium, non-starch polysaccharide, polycarbophil, chitin, pectin, partially hydrolyzed guar gum, beta-glucan, oligosaccharide, and fructooligosaccharide.

20. The orally adhering lozenge of claim 19, wherein the soluble dietary fiber comprises one or more of dextrin, partially hydrolyzed guar gum, inulin, and beta-glucan.

\* \* \* \* \*